United States Patent [19]

Nakagawa et al.

[11] Patent Number: 5,317,274
[45] Date of Patent: May 31, 1994

[54] HUMIDITY METER

[75] Inventors: Shiro Nakagawa, Chiba; Atsuko Tsuchida, Saitama, both of Japan

[73] Assignee: TDK Corporation, Tokyo, Japan

[21] Appl. No.: 986,688

[22] Filed: Dec. 8, 1992

[30] Foreign Application Priority Data

Dec. 13, 1991 [JP] Japan .............................. 3-110095[U]

[51] Int. Cl.$^5$ ............................................. G01W 1/00
[52] U.S. Cl. .................................. 324/678; 324/664; 324/676; 324/689; 73/29.01; 73/29.02; 73/335.02; 73/335.03; 73/335.04; 73/335.05; 338/35
[58] Field of Search ............... 73/29.01, 29.02, 335.02, 73/335.03, 335.04, 335.05; 324/606, 664, 665, 666, 667, 668, 669, 670, 676, 677, 678, 684, 685, 689; 338/35

[56] References Cited

U.S. PATENT DOCUMENTS

| | | | |
|---|---|---|---|
| 4,546,916 | 10/1985 | Tsuaki | 73/335.05 |
| 4,703,886 | 11/1987 | Kirby | 73/335.05 |
| 4,801,211 | 1/1989 | Yagi et al. | 73/335.05 |
| 4,915,816 | 4/1990 | Shakkottai et al. | 73/335.05 |
| 5,065,625 | 12/1991 | Nakagawa et al. | 73/336 |

*Primary Examiner*—Timothy M. McMahon
*Attorney, Agent, or Firm*—Martin Novack

[57] ABSTRACT

A humidity meter includes a humidity-frequency converter (2) which is essentially a pulse oscillator, the oscillation frequency of which depends upon the impedance of a humidity sensor (1), a differentiation circuit (3) and a wave-form shaping circuit (4) which essentially operate as a pulse width modulator for adjusting pulse width of an output pulse of the converter (2) for assuring a linear relationship between humidity and the output signal, and an integrator (6) for integrating the output of the pulse width modulator to provide an output signal as a DC level. A feedback path (5) is provided to apply the output signal to the pulse width modulator for assuring a linear output irrespective of the exponential characteristics of the humidity sensor. Said differentiation circuit (3) has a capacitor (31), a first variable impedance element (32) which is controlled by said feedback path, and a second variable impedance element (33) coupled in series with the first variable impedance element (32).

8 Claims, 7 Drawing Sheets

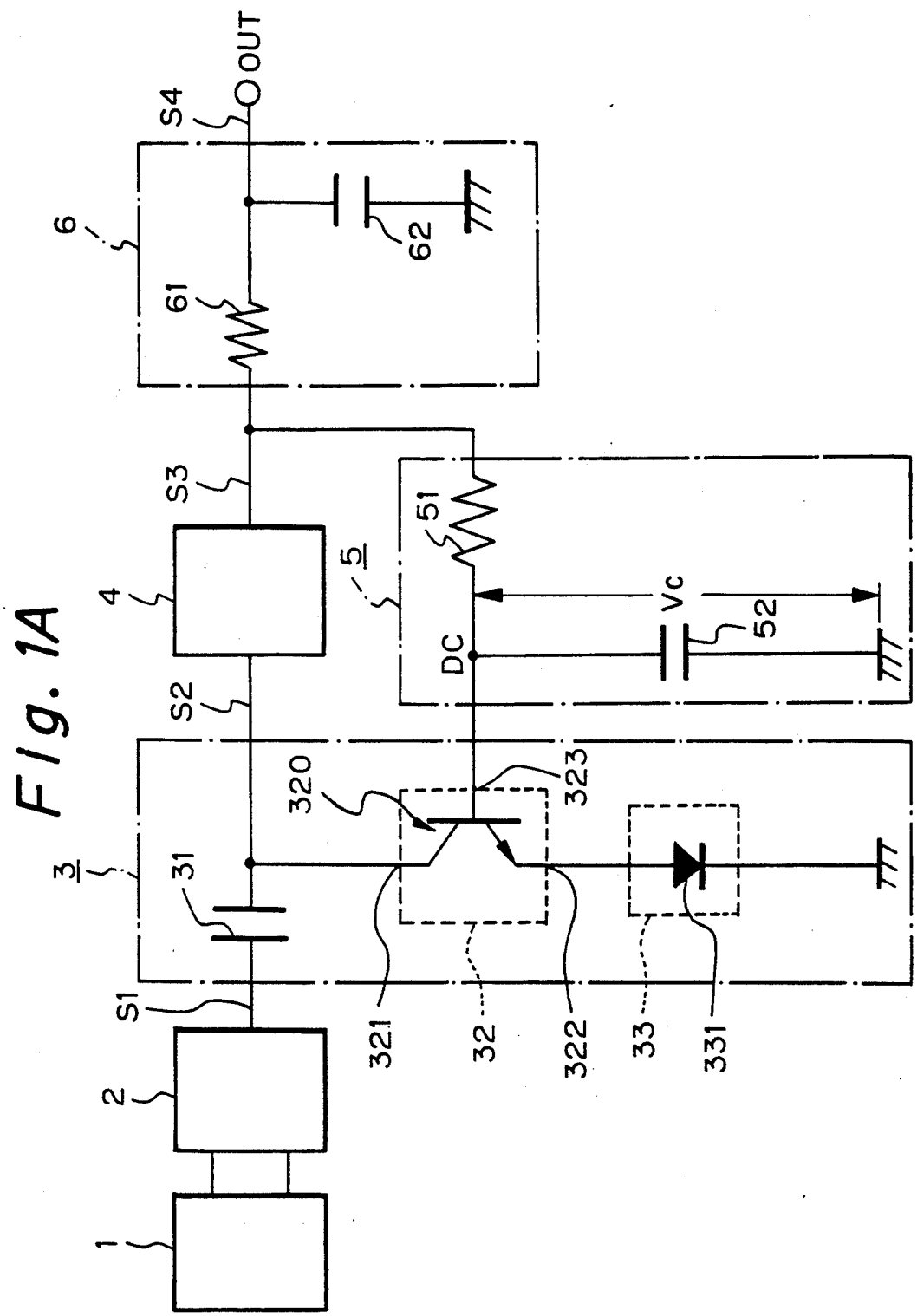

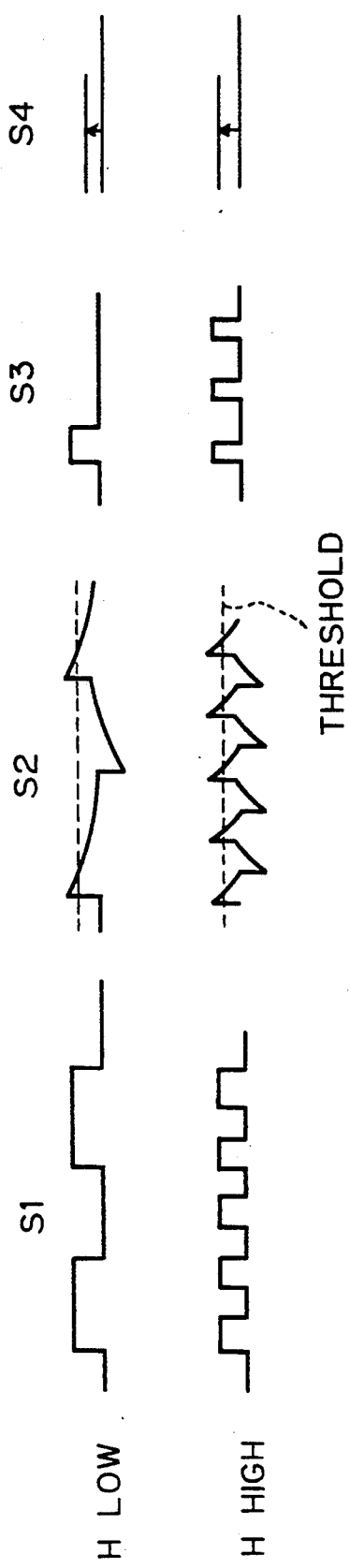

HUMIDITY METER

BACKGROUND OF THE INVENTION

The present invention relates to a humidity meter or a hygrometer which provides DC potential proportional to the measured relative humidity, in particular, relates to such a meter which improves linear relationship between humidity and output DC potential.

The present humidity meter is applicable to various kinds of electronics apparatuses, including a copying machine, a printer et al, and/or other field of application for visually indicating humidity.

Conventionally, a humidity sensor which provides electrical outputs relating to humidity has been known. One of them is an impedance change type humidity sensor, including a ceramics type humidity sensor or a polymer type humidity sensor. It is supposed that a water molecule couples with porous ceramics or porous polymer, which is ionized and provides electrical conductivity.

Although the impedance of a conventional humidity sensor relates to relative humidity, the relation between the impedance and the humidity is exponential. When the humidity is low, the impedance is high, and when the humidity is high, the impedance is very low. A prior electronic circuit is not sufficient for following the wide range of change of the impedance of the humidity sensor.

A prior humidity meter has a humidity-frequency converter which includes an impedance change type humidity sensor, and oscillates frequency relating to the impedance of said sensor. An output pulse of the humidity-frequency converter is applied to a frequency-voltage converter which comprises a differentiation circuit, a wave-form shaping circuit and an integrator, so that DC voltage relating to humidity is obtained at the output of the integrator.

However, said prior humidity meter has the disadvantages that it is impossible to provide linear output of humidity as the change of impedance for humidity is exponential, and the proper design of the differentiation circuit both for high humidity and low humidity is impossible.

One solution for solving the above disadvantages is shown in the U.S. Pat. No. 5,065,625. The important idea in the solution is to vary the time constant of said differentiation circuit through feed-back of the output of said integrator to said differentiation circuit.

However, we found that said prior art disclosed in the U.S. Pat. No. 5,065,625 has still disadvantages in;

a) The linearity of an output voltage is still insufficient, since a transistor which composes a differentiation circuit is insufficient for compensating exponential relations of a humidity sensor. In particular, a transistor can not provide high impedance between a collector and an emitter because of the presence of so-called $I_{CBO}$ when collector current is less.

b) An output voltage of humidity depends upon temperature, because a transistor which composes a differentiation circuit has some leak current ($I_{CBO}$) which depends upon temperature.

SUMMARY OF THE INVENTION

It is an object of the present invention to overcome the disadvantages and limitations of a prior humidity meter by providing a new and improved humidity meter.

It is also an object of the present invention to provide a humidity meter which can provide a linear output signal depending upon measured humidity in a wide range of humidity.

It is also an object of the present invention to provide a humidity meter which provides an output signal independent of ambient temperature.

The above and objects are attained by a humidity meter comprising; a humidity sensor (1) which provides impedance depending upon humidity to be measured; a humidity-frequency converter (2) for providing an alternate signal of frequency which depends upon the impedance of said humidity sensor (1); a differentiation circuit (3) coupled with output of said humidity-frequency converter (2) for providing differentiated signal of output of said humidity-frequency converter (2); a wave-form shaping circuit (4) coupled with output of said differentiation circuit (3) for providing an output pulse when an output of said differentiation circuit exceeds a predetermined threshold level; said differentiation circuit (3) and said wave-form shaping circuit (4) composing essentially a pulse width modulator for controlling pulse width of said alternate signal; a feed back means (5) for providing control potential at an output of said wave-form shaping circuit (4) to said differentiation circuit (3) to adjust time constant of said differentiation circuit (3); an integrator (6) coupled with output of said wave-form shaping circuit (4) for providing potential proportional to frequency and pulse width of output of said wave-form shaping circuit (4); an output terminal coupled with output of said integrator (6) providing measured humidity; said differentiation circuit (3) comprising a capacitor (31) with one end coupled with output of said humidity-frequency converter (2), and a series circuit of a variable impedance element (32) having a control input (323) coupled with said feed back means (5), and a non-linear impedance element (33), said series circuit being connected between the other end of said capacitor (31) and ground.

BRIEF DESCRIPTION OF THE DRAWINGS

FIG. 1A is a block diagram of a humidity meter according to the present invention, FIG. 1B shows operational waveforms of the humidity meter of FIG. 1A.

DESCRIPTION OF THE PREFERRED EMBODIMENTS

Figure 2:
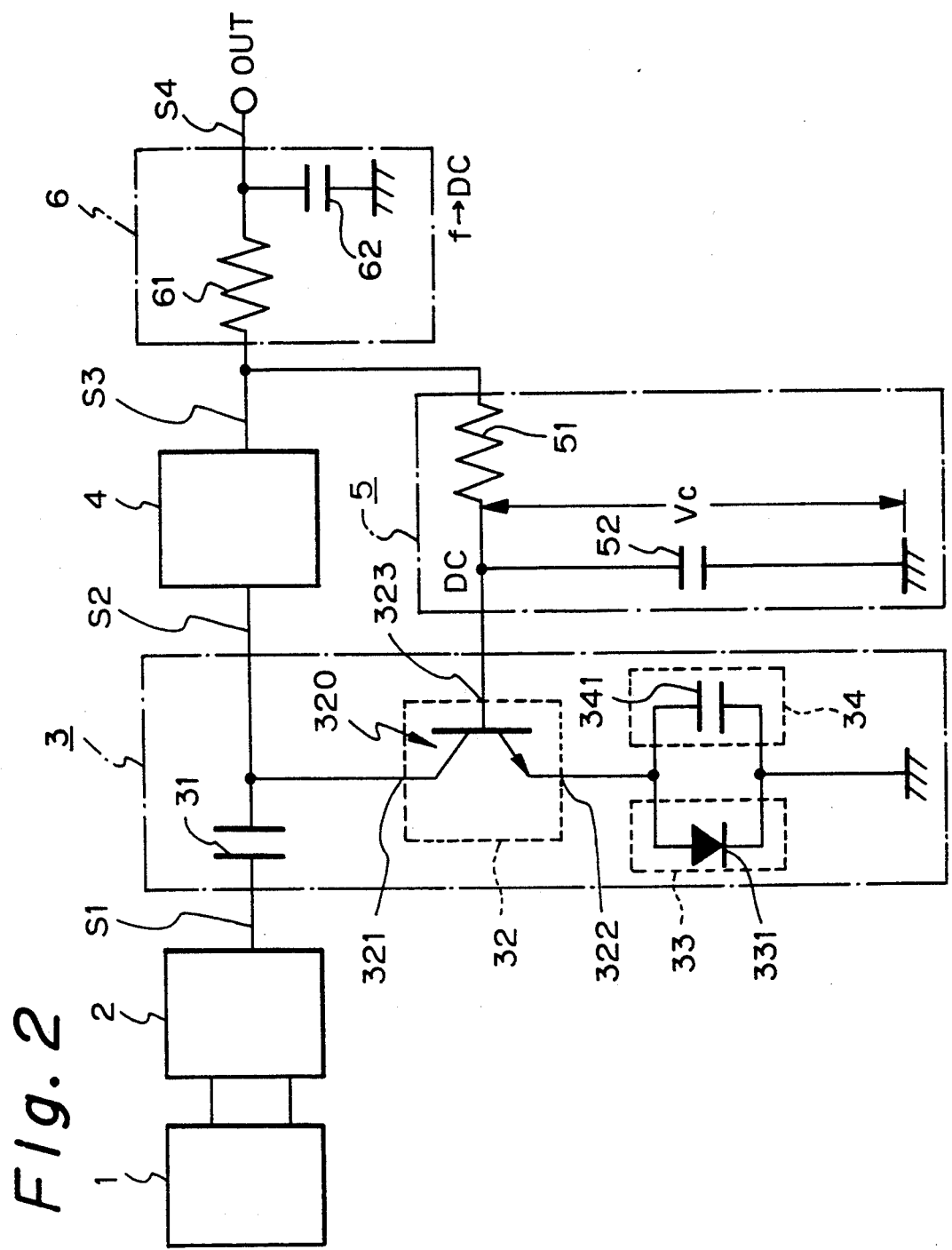
FIG. 2 is a block diagram of another embodiment of a humidity meter according to the present invention.

FIG. 1A shows a block diagram of the humidity meter according to the present invention. In the figure, the numeral 1 is a humidity sensor, 2 is an humidity-frequency converter (H-F converter), 3 is a differentiation circuit, 4 is a waveform shaping circuit, 5 a feedback circuit implemented by an integrator, and 6 is an integrator.

The humidity sensor 1 is, for instance, a high polymer type humidity sensor which changes impedance depending upon humidity so that the impedance is low for high humidity and the impedance is high for low humidity. The impedance is in the range for instance from $10^3 \Omega$ to $10^7 \Omega$.

The H-F converter 2 provides the frequency output signal S1. The frequency of the output signal depends upon the impedance of the sensor 1, or the humidity. When the impedance Zs of the sensor 1 is low the frequency is high, and when the impedance is high the frequency is low.

The differentiation circuit 3 has a capacitor 31 with an input of the same coupled with an output of the H-F converter 2, variable impedance element 32, and a non-linear impedance element 33. The elements 32 and 33 are connected in series to each other, and coupled between an output of the capacitor 31 and the ground so that the capacitor 31 and the series connected impedance elements compose a differentiation circuit.

The presence of a non-linear impedance element connected to the variable impedance element is the important feature of the present invention.

The variable impedance element 32 is implemented by a conventional transistor having a collector 321, an emitter 322, and a base 323. The impedance $Z_t$ between the collector 321 and the emitter 322 of the transistor 32 changes exponentially based upon the control voltage $V_c$ on the base 323.

The non-linear impedance element 33 is implemented for instance by a conventional diode 331. The impedance $Z_d$ of the non-linear impedance element 33 changes exponentially based upon the voltage across the element 33.

The differentiation circuit 3 provides an output signal S2 which is obtained by differentiating an input signal S1.

The wave-form shaping circuit 4 receives the differentiated signal S2, and provides the wave-form shaped output signal S3.

The differentiation circuit 3 and the wave-form shaping circuit 4 compose essentially a pulse width modulator. The pulse width of the wave-form shaping circuit 4 depends upon the frequency of the output of the H-F converter 2, or the humidity. The pulse width of the wave-form shaped output S3 depends upon the time constant of the differentiation circuit 3, and/or the threshold level of the wave-form shaping circuit 4. The present embodiment shows that the pulse width depends upon the time constant (or the impedance of the elements 32 and 33) of the differentiation circuit 3. The threshold level of the wave-form shaping circuit is fixed in the present embodiment.

The integrator 5 has a resistor 51 with one end coupled with an output of the wave-form shaping circuit 4, and a capacitor 52 coupled between the other end of the resistor 51 and the ground. The integrator 5 operates to integrate the wave-form shaped signal S3 to provide the control voltage $V_c$ to the base 323 of the transistor 32.

The integrator 6 which has a resistor 61 with one end coupled with an output of the wave-form shaping circuit 4, and a capacitor 62 coupled across the other end of the resistor 61 and the ground operates to provide DC (direct current) output signal S4 proportional to the measured humidity by integrating the pulse-modulated frequency signal S3.

Preferably, a temperature compensation element (not shown) having a thermister is coupled across an output of the integrator 6 and the ground so that the temperature dependency of the measured humidity is compensated for.

The humidity sensor 1 is excited with AC (alternate current) signal, since if it is exceited with DC signal, the sensor would be undesirably polarized. Further, it is preferable that the sensor is not heated by the exciting power. The H-F converter 2 is essentially an oscillator in which the oscillation frequency depends upon the impedance of the humidity sensor 1. Since the impedance of the sensor 1 varies exponentially with the humidity, the change of humidity by 10% changes the impedance of the sensor by even 100-500%. Also, the change of the temperature of the sensor by 0.1° C. would cause the error of the measured humidity by several %.

The differentiation circuit 3 having the varying time constant compensates the exponential relationships, and provides the linear output signal relating to the humidity. The time constant of the differentiating circuit 3 is adjusted by the feedback circuit or the integrator 5 which feed-backs the wave-form shaped signal S3.

FIG. 1B shows the operational wave-forms S1, S2, S3, and S4 in FIG. 1A. When the humidity is low, the frequency is low, and the final DC output level S4 is low. When the humidity is high, the frequency is high, and the final DC output level is high.

The diode 33 in the differentiation circuit 3 improves the compensation of the linear relationship between the humidity and the output DC potential. In our experiment, we found that the mere transistor 32 is insufficient to compensate the exponential relationship between humidity and impedance of a polymer type humidity sensor, in particular, when the humidity is low.

It should be noted that a transistor has leak collector current $I_{CBO}$ even when a transistor is in OFF state. Therefore, a transistor when it is used as a variable impedance element by a circuit between a collector and an emitter of a transistor can not have impedance larger than a predetermined value. This causes an error of measured humidity. Further, said leak current $I_{CBO}$ depends upon ambient temperature. This causes the temperature dependency of a humidity meter. Also, temperature dependency of base potential for making a transistor OFF state may cause an error of measured humidity and/or temperature dependency of measured humidity.

The non-linear impedance element, or the diode 33 adds supplemental non-linear impedance in series to the impedance element 32 so that when the potential (or the humidity) is low the impedance is higher than that of the element 32. The non-linear impedance element 33 is implemented by voltage drop in forward direction of a semiconductor diode. A diode has large impedance when an input voltage is low in forward direction, but less impedance when an input voltage is high. Preferably, a diode is a Shottky barrier diode.

The differentiated output of the differentiation circuit 3 is applied to the wave-form shaping circuit 4, which has a predetermined threshold level, and provide an output pulse (S3 in FIG. 1B) during an input level of the wave-form shaping circuit exceeds said threshold level. Therefore, the pulse width of the output pulse of the wave-form shaping circuit 4 depends upon the frequency, in other words, the pulse width depends upon the humidity measured by the humidity sensor 1. The output of the wave-form shaping circuit is applied to the integrator 6, which provides DC output signal (S4 in FIG. 1B) which is linearly proportional to humidity.

FIG. 2 shows another embodiment of the humidity meter according to the present invention. The same numerals in FIG. 2 show the same members as those in FIG. 1A. The feature of the embodiment of FIG. 2 resides in the non-linear impedance circuit 33, which has a parallel circuit of a diode 331 and an impedance compensation element 34 which is implemented by a capacitor 341.

The presence of a diode 331 in a differentiation circuit improves the linearity when humidity is low, or the input potential to the differentiation circuit is low. However, since a diode has some voltage drop in forward direction when potential across the diode is higher than a predetermined value, that voltage drop causes an error in humidity when humidity is high.

The capacitor 341 operates as a high-pass filter. As the voltage across the diode 331 is high the frequency applied to the diode 331 is also high. The capacitor 341 functions to reduce the voltage drop across the non-linear circuit 33 when humidity is high.

Preferably, the capacitance of the capacitor 341 is in the range from 1000 pF to 0.1 μF, and still preferably, the capacitance is between 6800 pF and 8200 pF.

As alternatives, a capacitor 341 may be substituted with a resistor, or a parallel circuit of a resistor and a capacitor.

Figure 3:
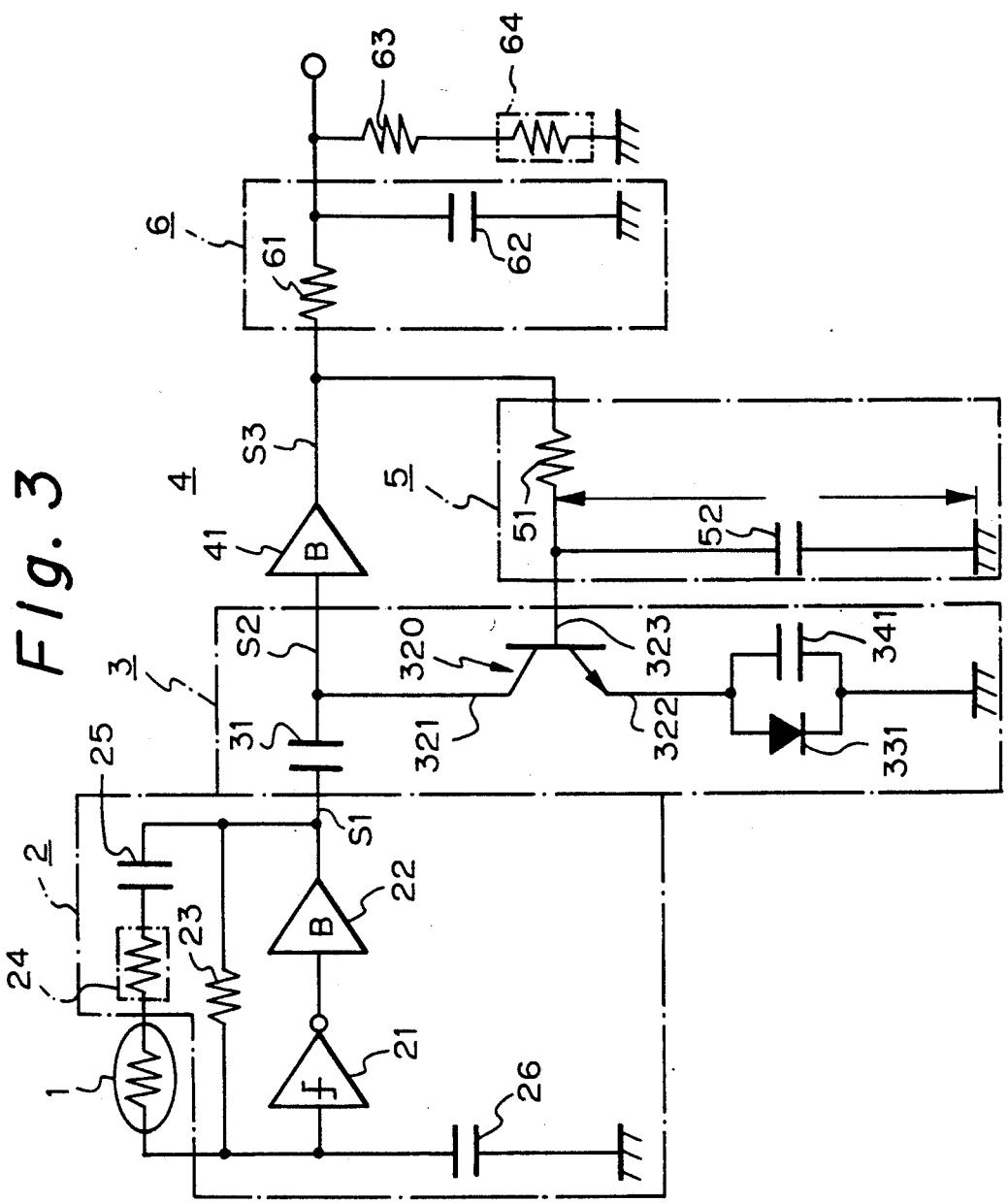
FIG. 3 is a detailed circuit diagram of a humidity meter shown in FIG. 2.

FIG. 3 shows a detailed circuit diagram of the humidity meter according to the present invention. The same numerals in FIG. 3 show the same elements as those in FIG. 1A or FIG. 2.

In FIG. 3, the H-F converter 2 has a Shimitt trigger circuit 21 (astable multivibrator), a buffer amplifier 22, a resistor 23, a thermister 24, a capacitor 25, and a capacitor 26. The humidity sensor 1 is connected in series to the thermister 24 and the capacitor 25. One end of the humidity sensor 1 is connected to an input of the Shmitt trigger circuit 21, and one end of the capacitor 25 is connected to an output of the buffer amplifier 22. The capacitor 26 is connected between an input of the Shimitt trigger circuit 21 and the ground. An output of the Shimitt trigger circuit 21 is connected to an input of the buffer amplifier 22. The resistor 23 is connected across an input of the Shmitt trigger circuit 21 and an output of the buffer circuit 22. The Shmitt trigger circuit 21 and the buffer amplifier 22 are implemented by a CMOS semiconductor element, or a TTL semiconductor element. The thermister 24 operates to compensates the temperature dependency of the humidity sensor 1. The capacitor 25 functions to prevent DC potential to the humidity sensor 1. The buffer amplifier 22 functions for wave-form shaping of the output of the Schmitt trigger circuit 21, and decrease the output impedance of the Schmitt trigger circuit 21.

The H-F converter 2 provides output frequency which depends upon the impedance of the humidity sensor 1, the resistor 23, the thermister 24, the capacitor 25, and the capacitor 26. As the impedance of the elements except the humidity sensor 1 is fixed, the output frequency of the H-F converter 2 is determined by the impedance of the humidity sensor 1 or the humidity.

The wave-form shaping circuit 4 in FIG. 3 is implemented by a buffer amplifier 41, which is implemented by a CMOS semiconductor element, or a TTL semiconductor element. The buffer amplifier 41 has a predetermined threshold level, and provides an output pulse when an input level exceeds the threshold level.

The embodiment of FIG. 3 has further an output circuit which comprises a resistor 63 and a thermister 64 connected in series to each other, and connected across an output terminal and the ground. The output circuit (63, 64) functions as a temperature compensation circuit to compensate the temperature dependency of the measured humidity.

Other circuits in FIG. 3 are the same as those in FIG. 2.

It should be noted of course that an output circuit (63, 64) is used also in the embodiment of FIG. 1A.

Figure 4A:
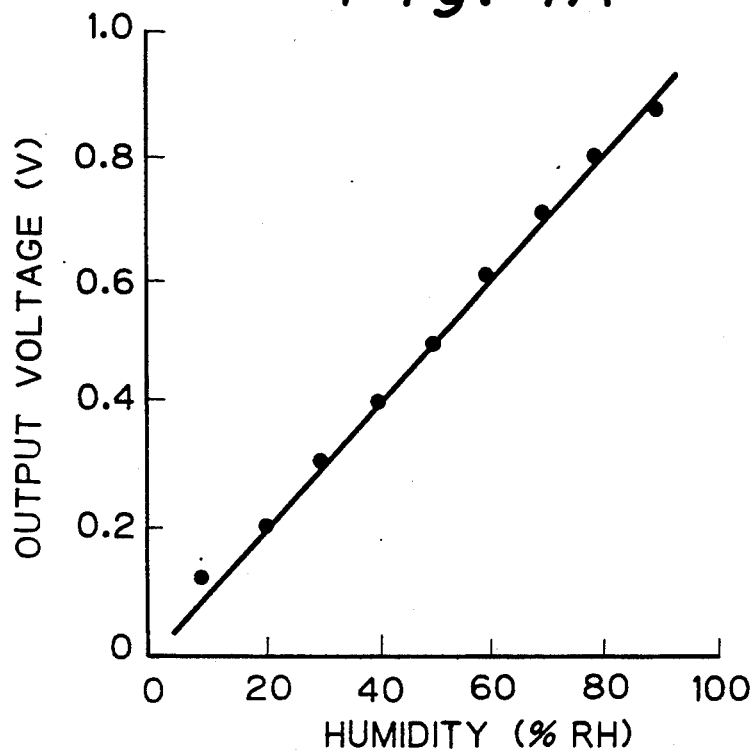
FIG. 4A shows curves between output voltage and humidity according to the present invention.
Figure 4B:
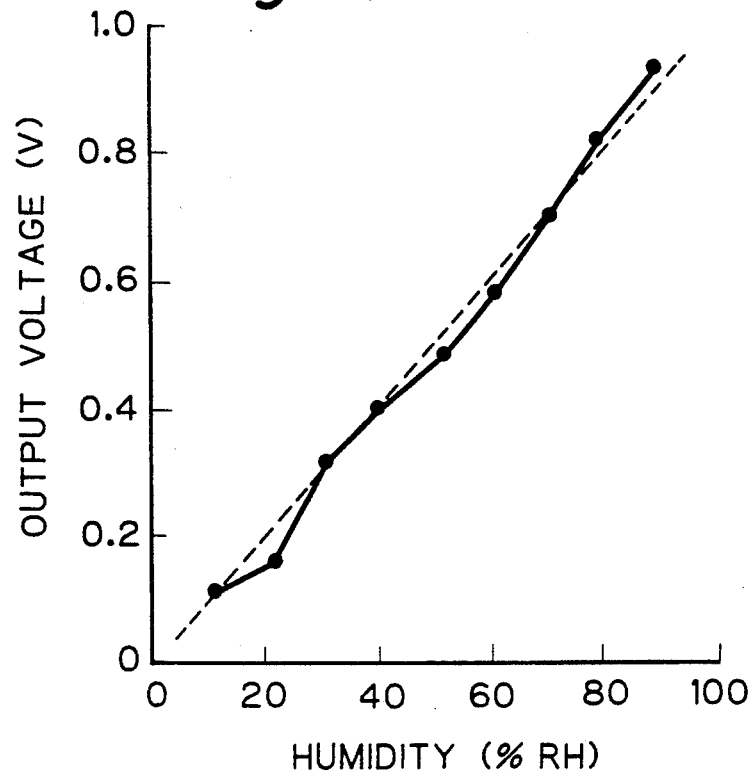
FIG. 4B shows curves between output voltage and humidity in the prior art shown in the U.S. Pat. No. 5,065,625.

FIG. 4A and FIG. 4B show the curves between humidity and output voltage of the present humidity meter (FIG. 4A), and the prior art (FIG. 4B) disclosed in the U.S. Pat. No. 5,065,625.

In those figures, the horizontal axis shows relative humidity, and the vertical axis shows output voltage in DC level. FIG. 4A shows the characteristics of the humidity meter of FIG. 3. It should be noted in those curves that the linearity that the humidity is lower than 70% is improved by the presence of a diode 331, and the linearity that the humidity is higher than 70 % is improved by the presence of the capacitor 341. The total linearity of FIG. 4A is considerably improved as compared with that of FIG. 4B.

Figure 5A:
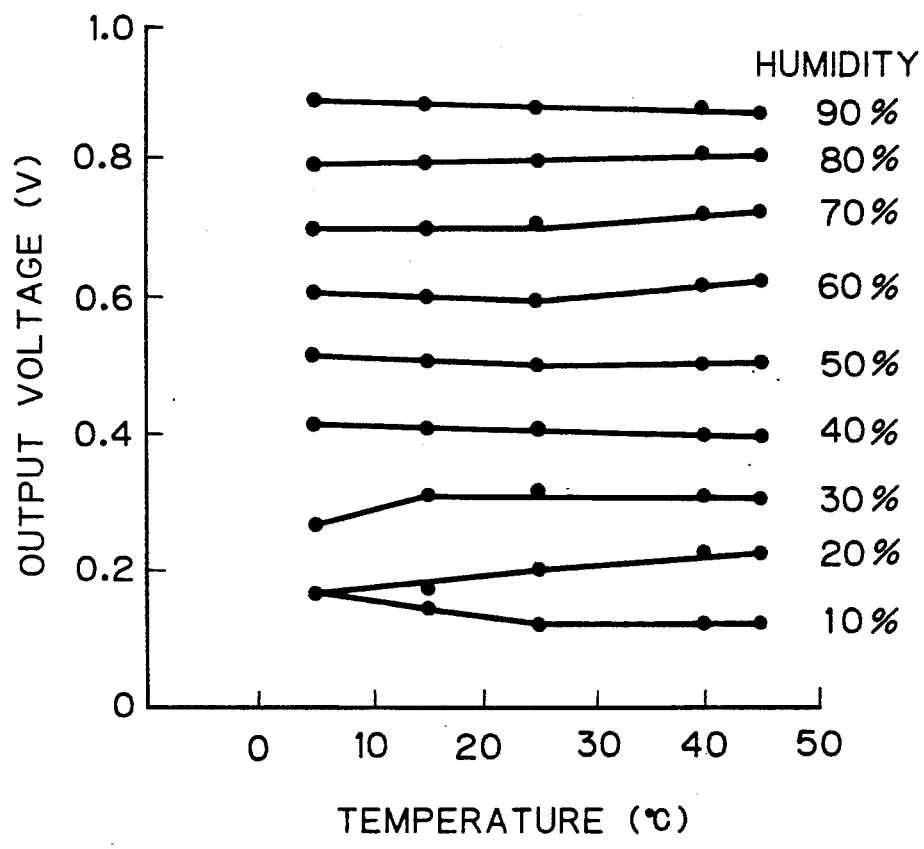
FIG. 5A shows curves between output voltage and ambient temperature with parameter of humidity according to the present invention.
Figure 5B:
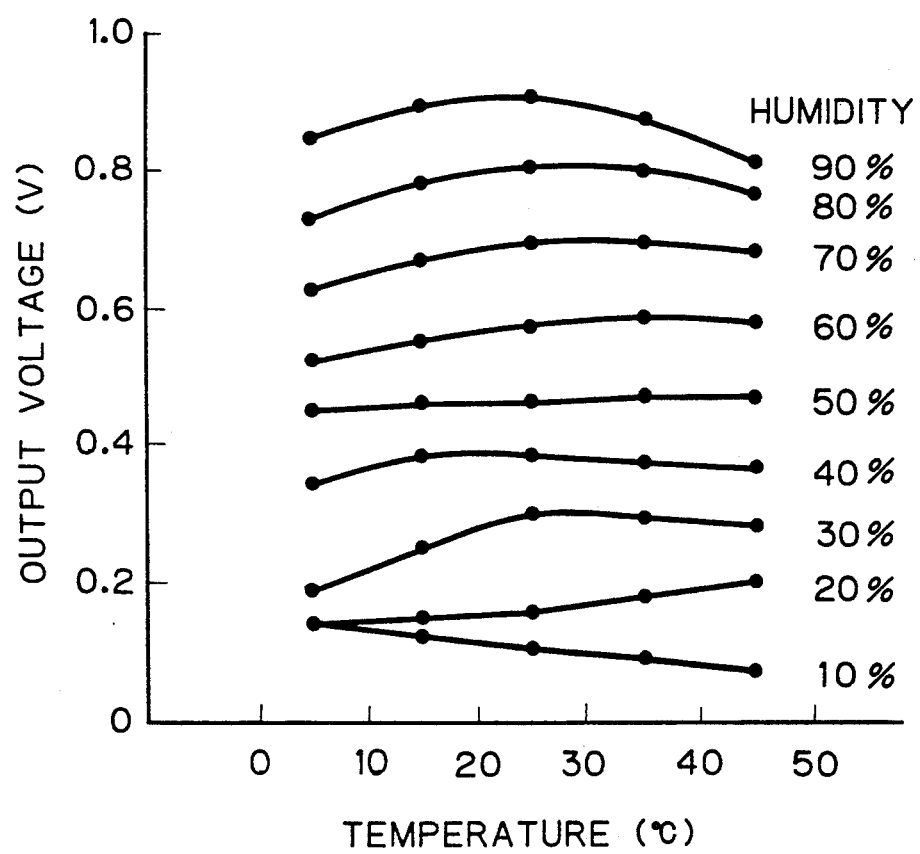
FIG. 5B shows curves between output voltage and temperature with parameter of humidity in the prior art shown in the U.S. Pat. No. 5,065,625.

FIG. 5A and FIG. 5B show the curves showing temperature dependency of the measured humidity. FIG. 5A shows the curves of the present invention (FIG. 3) having a diode 331, and a capacitor 341 together with an output thermister 64, and FIG. 5B shows the curves of a prior art (U.S. Pat. No. 5,065,625) which has also an output thermister. In those figures, the horizontal axis shows room temperature in °C., and the vertical axis shows output DC voltage. The parameter is relative humidity in %.

In comparing FIG. 5A with FIG. 5B, the temperature dependency of the present humidity meter is much improved, in particular, when the temperature and the humidity are high.

As described above in detail, according to the present invention, a diode is inserted in series to a transistor in a differentiation circuit. And, in one modification, a capacitor is coupled across said diode. The diode compensates the error of a transistor due to the presence and fluctuation of leak collector current $I_{CBO}$ and/or base potential for causing a transistor OFF state.

From the foregoing, it will now be apparent that a new and improved humidity meter has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A humidity meter comprising;
   a humidity sensor (1) which provides impedance depending upon humidity to be measured,
   a humidity-frequency converter (2) for providing an alternating signal of frequency which depends upon the impedance of said humidity sensor (1),
   a differentiation circuit (3) coupled with output of said humidity-frequency converter (2) for providing a differentiated signal by differentiating of output of said humidity-frequency converter (2).

a wave-form shaping circuit (4) coupled with output of said differentiation circuit (3) for providing an output pulse when an output of said differentiation circuit exceeds a predetermined threshold level, said differentiation circuit (3) and said wave-form shaping circuit (4) comprising a pulse width modulator for controlling pulse width of said alternating signal, a feed back means (5) for providing a control potential at an output of said wave-form shaping circuit (4) to said differentiation circuit (3) to adjust the time constant of said differentiation circuit (3), an integrator (6) coupled with the output of said wave-form shaping circuit (4) for providing a potential proportional to frequency and pulse width of the output of said wave-form shaping circuit (4), an output terminal coupled with the output of said integrator (6) providing measured humidity, said differentiation circuit (3) comprising an capacitor (31) with one end coupled with the output of said humidity-frequency converter (2), and a series circuit of a variable impedance element (32) having a control input (323) coupled with said fee back means (5), and a non-linear impedance element (33) having larger impedance when the potential applied thereto is low as compared to when the potential applied thereto is high, said series circuit being connected between the other end of said capacitor (31) and ground.

2. A humidity meter according to claim 1, wherein said variable impedance element (32) is a transistor which provides variable impedance between a collector and an emitter of the transistor according to said control potential applied to a base of the transistor, and said non-linear impedance element (33) is a diode.

3. A humidity meter according to claim 2, wherein said transistor is a bipolar transistor, and said diode is coupled with said transistor so that the current direction between a collector and an emitter of the transistor coincides with the forward direction of the diode.

4. A humidity meter according to claim 2, wherein a capacitor (34) is coupled across said diode.

5. A humidity meter according to claim 4, wherein said capacitor (34) has capacitance in the range from 1000 pF to 0.1 $\mu$F.

6. A humidity meter according to claim 1, wherein a temperature compensation circuit having a thermister (62) is coupled across an output terminal and ground.

7. A humidity meter according to claim 1, wherein said feed back means is an integrator having a resistor (51) with one end coupled with the output of said wave-form shaping circuit (4), and a capacitor (52) coupled with the other end of said resistor (51) and ground, the junction of said resistor and said capacitor providing said control potential.

8. A humidity meter according to claim 2, wherein said diode is a Shottky barrier diode.

* * * * *